大,
United States Patent [19]

Marconi et al.

[11] 4,243,776

[45] Jan. 6, 1981

[54] PREPARATION OF NON-THROMBOGENIC POLYMERIC MATERIAL ARTICLE WITH PLATELET ANTI-AGGREGATIVE AGENT

[75] Inventors: Walter Marconi, San Donato Milanese; Francesco Pittalis; Francesco Bartoli, both of Rome; Franco Morisi, San Giovanni In Persiceto, all of Italy

[73] Assignee: Snamprogetti S.p.A., Milan, Italy

[21] Appl. No.: 917,568

[22] Filed: Jun. 21, 1978

[30] Foreign Application Priority Data

Jul. 27, 1977 [IT] Italy .............................. 26191 A/77

[51] Int. Cl.³ .............................................. C08G 69/46
[52] U.S. Cl. .................................... 525/420; 525/326; 525/329; 525/375; 525/437; 525/453; 536/56; 536/61; 536/76; 536/85

[58] Field of Search ..................... 536/56, 61, 76, 85; 525/329, 326, 375, 420, 437, 453

[56] References Cited

U.S. PATENT DOCUMENTS

| | | | |
|---|---|---|---|
| 3,371,069 | 2/1968 | Miyamae et al. ..................... | 528/311 |
| 3,711,583 | 1/1973 | Sklar ..................................... | 528/311 |
| 3,907,755 | 9/1975 | Margraff et al. ..................... | 528/311 |
| 3,970,597 | 7/1976 | Sokolovsky et al. ................. | 528/333 |
| 3,994,866 | 11/1976 | Lund et al. ........................... | 528/311 |
| 4,069,105 | 1/1978 | Singh .................................... | 528/311 |

*Primary Examiner*—Harold D. Anderson
*Attorney, Agent, or Firm*—Morgan, Finnegan, Pine, Foley & Lee

[57] ABSTRACT

Biocompatible articles are obtained by treating a polymeric material with a hydrolyzing agent on its surface and covalently binding thereon a biological agent, such as an anti-platelet-aggregation agent.

6 Claims, No Drawings

PREPARATION OF NON-THROMBOGENIC POLYMERIC MATERIAL ARTICLE WITH PLATELET ANTI-AGGREGATIVE AGENT

This invention relates to novel biocompatible polymeric articles and a method for making said articles.

In the technical literature, and more particularly in the U.S. patent application Ser. No. 885,195 filed on Mar. 10, 1978 it has been disclosed that it is possible to prepare biocompatible materials by methods which consist in occluding appropriate biological materials, more particularly anti-clotting agents or platelet anti-aggregative agents, in polymeric materials.

More particularly, the methods comprise the steps of dispersing in solutions which contain the polymer capable of producing fibres, solutions which contain the biological agents. The emulsions which are obtained are dry-spun or wet-spun to give fibres which are a physical solution of both the polymer and the agent. Such agents are capable of displaying their specific activity also in the biocompatible polymeric articles of this invention.

It has now been found, and this is the principal subject matter of the present invention, that it is possible to chemically bind the biological agents, more particularly anti-aggregative agents for platelets, to the surfaces of polymers, with the concurrent formation of stable covalent bonds, without impairing the properties and the specific biological activity, the latter remaining unaltered and rendering the polymer biocompatible.

The formation of the stable covalent bond requires that the polymeric material contains reactive functional groups that are capable of reacting with the biological agents by means of a bifunctional compound that is capable of reacting with the polymeric supporting material.

Polymers that can be used in the practice of the invention include polyesters, polyamides and cellulose polymers which under mild hydrolysis will yield reactive groups that will chemically react with the anti-aggregative agent.

An additional possibility is to prepare polymers having functional groups available for direct reactions or exchange reactions (formation of amide bonds, ester bonds and the like) with the anti-aggregative agent.

Lastly, it is possible to synthesize polymers wherein the anti-aggregative agents are reacted into the polymer in the polymeric chain as a repeating unit in the main chain and as an appendant group bound to a functional group in the monomeric unit.

Thus, for example, polyurethanes can be obtained starting from platelet-anti-aggregative agents containing hydroxyl groups, and starting from di-isocyanates.

Anti-aggregative agents containing hydroxyl groups can be used for functionalizing the starting monomers in order to obtain substituted polymers such as polyacrylates, polyesters, polyamides and others.

Anti-aggregative agents which can be used according to the present invention are 4,5-diphenyl-2-bis (2-hydroxyethyl) aminooxazole, 4,8-dipiperidino-2,6-diethanolamino-pyrimido-(5,4 d) pyrimidine, or dipyridamol, sulfinpyrazone and, in general, platelet-anti-aggregative agents having reactive groups or susceptible of being functionalized without losing their pharmacological properties.

The present method leads to the formation of biocompatible fibres, that is, fibres capable of being inserted into a living organism or anyhow capable of being placed into contact with blood without involving hemorrhage hazards or toxicity (as it occurs in the case in which soluble anti-coagulants are used) and without involving the hazard of thrombi formation.

The materials which can be prepared with such fibres can be, for example, tubes, membranes, artificial limbs, various protheses, sounds for medical use.

The instant method can be used either on the material already shaped in the desired outline, or prior to the shaping of the prosthetic article by reacting the platelet-anti-aggregative material with the polymer concerned in the form of powder, chips, pellets and otherwise.

The invention will be described in more detail by the following examples which are by no means limitations thereof.

EXAMPLE 1

250 mls of anhydrous toluene have been saturated at about 4° C. with about 190 g of $COCl_2$. This solution has been supplemented with 100 g of 4,5-biphenyl-2-bis-(2-hydroxyethyl)-amino oxazole, prepared according to the methods disclosed by the literature: V. Rosnati, E. Marchetti, C. Mattalia—Journal Medical Chemistry, 11, page 1092-1093, (1968).

The added compound dissolved slowly as the reaction went on. After 30 mins. the mixture was thoroughly clear. After 2 hrs. the excess phosgene has been evaporated off, the solvent has been exhausted by a vacuum pump and there have been obtained 130 g of a white solid residue. Such a residue has been subjected to spectroscopical analysis and has been found to be bis-chloroformate of the starting compound.

2 g of such a product have been dissolved in 30 mls of anhydrous acetone and, in such solution there have been dipped 5 m of nylon thread (diameter: 150 microns) which had previously hydrolyzed superficially with 3-N HCl at 30° C. and then washed with 1 N NaOH and water. The reaction has been allowed to proceed during 30 mins., whereafter the nylon thread has been withdrawn from the reaction mixture, washed with acetone and then examined under a UV lamp.

The thread was intensely fluorescent due to the presence on its surface of the derivative of the 4,5-diphenyl-2-bis-(2-hydroxyethyl)-amino oxazole chemically bonded to the aminic groups of the hydrolyzed nylon.

A teflon (Reg. T.M.) catheter (Wallace intravenous type, 30 cm. long, inside dia. 0.69 mm, outside dia. 1.14 mm) has been coated by a cellulose triacetate film by dipping the sound in a solution of polymer in 2% wt/wt methylene chloride containing 4,5-diphenyl-2bis-(2-hydroxyethyl)-amino oxazole in an amount equal to 10% relative to the triacetate. About the thus obtained sound there have been wound the 5 meters of nylon thread with the anti-aggregative agent chemically bound thereto so as to obtain an even coating of the whole sound throughout. A comparison sound has been prepared with an identical nylon thread sample, 5 m long which, obviously was untreated. The two sounds have been inserted in the femural veins of a medium size dog under total anaesthesia by Penthotal, free respiration. A collateral branch of the femural vein has been isolated and a sound has been introduced its whole length throughout so that a major section of the sound was floating in the iliac vein and in the vein cava inferior.

The end of the sound has been tied to the collateral branch of the femural vein and covered by muscle bundles. Lastly, the wound has been sutured. In the same way, the second sound has been introduced into the other femural vein of the animal. Before and after the operation, heparin has been administered to the animal to prevent vascular thrombi due to the surgical lesions. The sounds have been left inserted for 30 days at the end of which the animal has been sacrificed and the sounds withdrawn. The sound with the nylon thread to which 4,5-diphenyl-(2bis-(2-hydroxyethyl) amino oxazole had been chemically bound has been withdrawn clean and absolutely deprived of thrombi. Also the vascular wall was found unaffected in the post mortem examination. The sound with the untreated nylon thread was covered, conversely, by a number of thrombi.

EXAMPLE 2

250 mls of anhydrous toluene have been saturated at about 4° C. with about 380 g of $COCl_2$. To the solution there have been added 160 g of 4,8-dipiperidino-2,6-diethanolamino-pirimido (5,4 d) pirimidine (dipiridamol).

The compound has become slowly dissolved as the reaction went on. After about 40 mins. the solution was thoroughly clear and, after two hours the excess phosgene has been evaporated off and the solvent has been exhausted by a vacuum pump. There have been obtained 110 g of a solid yellow residue which, at the spectroscopical analysis proved to be the chloroformyl derivative of the starting compound.

According to the procedure disclosed in Example 1, the as obtained product has been reacted with 5 m of nylon thread (150 micron dia.) which had previously been hydrolyzed.

The biocompatibility of the thus obtained thread as compared with an identical sample of untreated nylon thread has been assayed in vivo, on test dogs, using intravenous sounds prepared and employed according to the procedure set forth in Example 1. Also in this case the treated sound proved, after one month, to be devoid of thrombi, while the reference sound displayed conspicuous thrombi on its surface.

EXAMPLE 3

3 m of nylon tube (O.D. 9 mm, I.D. 7 mm) have been subjected to a partial hydrolysis in the inner wall surface by having a solution of 3-N HCl flowing therethrough for 40 mins. at 30° C. Once the hydrolysis has occurred, the tube has been washed, firstly with 1-N NaOH, then with water and eventually with acetone. At this stage a 3% solution in acetone of 4,5-diphenyl-2bis-(2-hydroxyethyl) amino oxazole has been recycled during one hour therethrough, the compound having been subjected to chloroformylation according to the procedure reported in Example 1. On completion of the reaction the tube has carefully been washed with acetone and dried. The confirmation of the chemical attack undergone by the compound was an intense fluorescence on the inner tube wall, which could be seen at the UV lamp. On tube sections treated with 4,5-diphenyl-2bis-(2hydroxyethyl) amino oxazole and on tube sections of an identical untreated nylon tube the platelet adhesiveness test has been performed. The method by A. J. Hellem has been followed ("Platelet adhesiveness in von Willebrand's disease—A study with a new modification of the glass bead filter method, Scand. J. Haemat., 7, 374, (1970)), using native blood of a healthy subject, drawn and passed through the tubes subjected to the test by means of a pump giving a rate of flow of 4 mls/min.

Platelet counts have been effected before and after the flow of the blood through the nylon tubes.

The counts have been made by collecting blood samples in aqueous solution containing EDTA (bipotassic salt) at the concentration of 6 g in 10 ml.

The platelet count has been made with a phase contrast microscope according to the procedure by Brecher and Cronkite (Morphology and enumeration of human blood platelets, J. Appl. Physiology, 3, 365, (1950)).

In the case of untreated nylon tubes the platelet adhesiveness was 56.5%.

Conversely, in the case of nylon tubes with the derivative of 4,5-diphenyl-2bis-(2-hydroxyethyl) amino oxazole which were chemically attacked, no appreciable decrease of the platelet number has been observed.

EXAMPLE 4

A conventional dialysis tube made of cellulose (Dia. 6 mm) has been thoroughly washed with water and then with acetone. At this stage, the tube has been dipped in a 3% solution in acetone of 4,5-diphenyl-2bis-(2-hydroxyethyl) amino oxazole subjected to chloroformylation according to the procedure indicated in Example 1. To the solution, triethylamine has been added as an acid acceptor. After one hour of reaction at room temperature, the tube has been washed, first with acetone and then with water. An intense fluorescence at the UV lamp confirmed the occurrence of the attack of the 4,5-diphenyl-2bis-(2-hydroxyethyl) amino oxazole derivative on the cellulose hydroxyls.

On a sample of the thusly obtained tube and on a sample of the untreated tube, the platelet adhesiveness test has been conducted. The procedure was that of Example 2. It has been observed that, while in the untreated tube the adhesiveness was as high as 61%, in the case of the tube treated with the derivative of 4,5-diphenyl-2bis-(2-hydroxyethyl) amino oxazole which had been attacked superficially, no appreciable decrease of the platelets was ascertained.

EXAMPLE 5

Nylon 6—6 tablets (thickness 250 microns, length 2 cm, height 1 cm) have superficially been hydrolyzed with 4-N HCl at 30° C. for 20 mins. Once the hydrolysis has taken place, the platelets have been washed, first with a 1-N solution of NaOH, then with water and finally with acetone.

At this stage they have been dipped in a 3% solution in anh.acetone of 4,5-diphenyl-2bis-(2-hydroxyethyl) amino oxazole which had previously been chloroformylated according to the procedure set forth in Example 1. After one hour the tablets have been removed from the reaction environment and thoroughly washed with acetone. An intense fluorescence could be seen at the UV lamp and confirmed the occurrence of the attack of the compound on the surface amine groups of the hydrolyzed nylon. Similar comparison tablets have been prepared, which were made of untreated nylon.

The tablets having the chemical compound chemically attacked on the surface have been inserted subcutaneously in test rabbits.

On the tablets two side bores had been formed to permit their fastening by suture stitches to the subcutaneous muscular bundles.

Untreated reference tablets have likewise been inserted. Lastly, the wounds have been sutured. After 30 days the tablets have been withdrawn. In the case of the tablets which had been subjected to the superficial chemical attack of the 4,5-diphenyl-2bis-(2-hydroxyethyl) amino oxazole no inflammatory reactions of the connective tissues have been observed. Conversely, the untreated tablets were surrounded by a wide scar debris area.

EXAMPLE 6

8 g of 4,5-diphenyl-2bis-(2hydroxyethyl) amino oxazole have been added to 30 ml of chlorobenzene and heated to a gentle boil only. To this solution, 16 g of hexamethylenediisocyanate, dissolved in 10 mls of chlorobenzene, have been added.

After a 4 hour reaction, the solution has been cooled and the solvent exhausted by means of a vacuum pump. The residue, dissolved in dimethylformamide has been precipitated with methanol, collected on a filter and dried.

The as obtained product is a polyurethan which is soluble in chlorinated solvents such as methylene chloride.

Intrinsic viscosity measurements have been taken of the polymer dissolved in meta cresol. The viscosity at 30° C. at the concentration of 0.5% (vol/vol) was $\eta_{in} = 0.47$ dl/g.

2 grams of the product have been dissolved in 50 mls of methylene chloride. In this solution has been dipped an intravenous Teflon (Reg. T.M.) catheter such as that described in Example 1. On the catheter removed from the polymer solution, there is formed, by slow evaporation of the solvent at 4° C., a polymer film which coated with the catheter surface evenly.

According to the procedure described in Example 1, the sound thus obtained and a reference sound (untreated) have been inserted in test dogs. After 30 days the sound coated by the polyurethan the preparation of which has been outlined above, has been withdrawn clean, whereas the reference sound was completely covered by thrombi.

We claim:

1. A method for rendering an article made from a polymeric material non-thrombogenic comprising chemically binding a platelet anti-aggregative agent selected from the group consisting of 4,5-diphenyl-2-bis-(2-hydroxyethyl)amino oxazole and 4,8-dipiperidino-2,6-diethanolamino-pyrimido-5, 4-d pyrimidine to the surface of said polymeric material.

2. The method as defined in claim 1 wherein said polymeric material is selected from the group consisting of nylon polyamides, cellulose polymers, and polyacrylates.

3. A method as defined in claim 1 wherein the platelet anti-aggregative agent is chemically bound to the polymeric material by contacting a polymeric material that has been subjected to hydrolysis with the platelet aggregative agent.

4. A method as defined in claim 1 wherein the polymer is a nylon polyamide and the platelet anti-aggregative agent is 4,5-diphenyl-2-bis-(2-hydroxyethyl) amino oxazole.

5. A biocompatible sound, tube, membrane or artificial organ made by the process of claim 1.

6. A biocompatible sound, tube, membrane or artificial organ made by the process of claim 4.

* * * * *